United States Patent [19]
McDonald

[11] Patent Number: 5,193,684
[45] Date of Patent: Mar. 16, 1993

[54] TAMPON DISPOSAL UNIT

[76] Inventor: Gary L. McDonald, 104 S. Ora, Pryor, Okla. 74361

[21] Appl. No.: 915,221

[22] Filed: Jul. 20, 1992

[51] Int. Cl.$^5$ ............................................. A61F 13/34
[52] U.S. Cl. ................................... 206/581; 206/438; 206/440; 206/466; 206/823
[58] Field of Search ................ 141/114; 206/438, 440, 206/581, 461, 462, 466, 812, 823

[56] References Cited

U.S. PATENT DOCUMENTS

| | | | |
|---|---|---|---|
| 3,035,578 | 5/1962 | Elmore | 128/290 |
| 4,373,631 | 2/1983 | Friese et al. | 206/438 |
| 4,705,171 | 11/1987 | Eldridge | 206/440 X |
| 4,735,316 | 4/1988 | Froidh et al. | 206/438 |
| 4,765,477 | 8/1988 | Froidh et al. | 206/438 |
| 4,838,327 | 6/1989 | Ambler et al. | 141/114 |
| 4,848,572 | 7/1989 | Herrera | 206/438 X |
| 4,857,066 | 8/1989 | Allison | 206/438 X |
| 5,088,993 | 2/1992 | Gaur | 206/438 X |

*Primary Examiner*—David T. Fidei
*Assistant Examiner*—Jacob K. Ackun, Jr.
*Attorney, Agent, or Firm*—Robert K. Rhea

[57] ABSTRACT

A sanitary item disposal unit is formed by a disposable bag having an accordion pleated collapsible wall which unfolds in a longitudinal extending action of the bag as the sanitary item is withdrawn from a cavity, through a central aperture in a support panel, into the bag. Respective end portions of the bag support panel are pressure tape sealed for closing the bag and disposal of the sanitary item with its bag container.

3 Claims, 2 Drawing Sheets

TAMPON DISPOSAL UNIT

BACKGROUND OF THE INVENTION

1. Field of the Invention

This invention relates to sanitary items and more particularly to disposal of tampons.

The disposal of sanitary items sometimes creates a problem for the reason satisfactory receptacles or facilities are many times not readily available.

This is particularly true in public restrooms where traffic may be heavy and where some individuals tend to become careless or exercise insufficient care in the disposal of sanitary items because of the inconvenience.

This invention eliminates such problems, in part at least, by providing an easily used relatively small collapsed container which may be conveniently carried in a pocket or a purse.

2. Description of the Prior Art

The most pertinent patent is believed to be U.S. Pat. No. 4,838,327 issued Jun. 13, 1989 to Ambler, et al for Receptacle Bag Assembly. This patent discloses a sealable bag having an insert slidably positioned therein for restraining the complete withdrawal of the insert from the bag. The insert may be arcuately flexed lengthwise in a manner to substantially open the bag and allow for the disposal of materials thereinto.

Other patents relating to the disposal of sanitary items are directed more particularly to the disposal of sanitary napkins. U.S. Pat. No. 3,035,578 issued May 22, 1962 to Elmore for Sanitary Napkin Cover is considered a good example of the further state-of-the-art. This patent discloses a sheet attached to an absorbent material sanitary napkin which may be unfolded and used as a wrapper for the disposal of the sanitary napkin.

This invention is distinctive over these and other patents relating to sanitary item disposal by providing a bag-type container arranged in a wall collapsible form and joined with a shield which may be placed over the cavity which surrounds the item as it is removed and forms a pair of flaps for sealing the bag for disposal of the entire unit in a receptacle provided in most restrooms.

SUMMARY OF THE INVENTION

A generally ovate flexible front or forward sheet is bonded by its perimeter edges to a similar center sheet. Both sheets are provided with a central aperture and a plurality of radial slits around its aperture.

An elongated flexible and collapsible accordion wall tube or bag has its front or forward end closed by a disk interposed at its peripheral edge between the front and center sheets and is provided with a plurality of radial slits extending outwardly from its center. The bag wall open end is secured to the center sheet around the perimeter of its aperture.

A flexible inward or backing sheet similarly ovate in shape having a central opening and radial slits is similarly bonded by its perimeter with the center sheet opposite the front sheet.

A length of soft material forming a towel elongated in folded configuration, is secured at one end portion to one end portion of the three sheets on the major axis.

A short strap-like section of material extends transversely of the towel on the inner or back sheet adjacent its minor axis to maintain the opposite end portion of the towel in place.

The principal object of this invention is to provide a convenient economical easily operated disposable package for the disposal of sanitary items.

DESCRIPTION OF THE PREFERRED EMBODIMENTS

Figure 1:
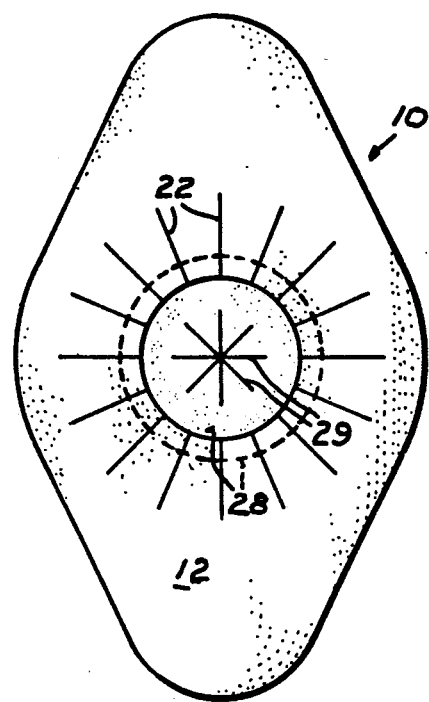
FIG. 1 is a front elevational view of the device.

Like characters of reference designate like parts in those figures of the drawings in which they occur.

Figure 2:
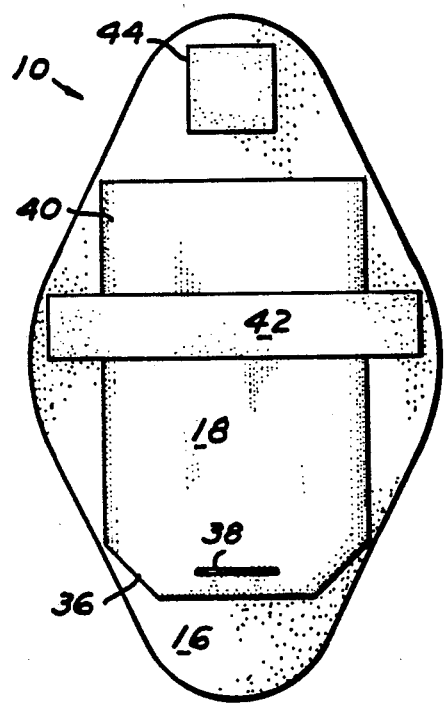
FIG. 2 is a back elevational view.
Figure 3:
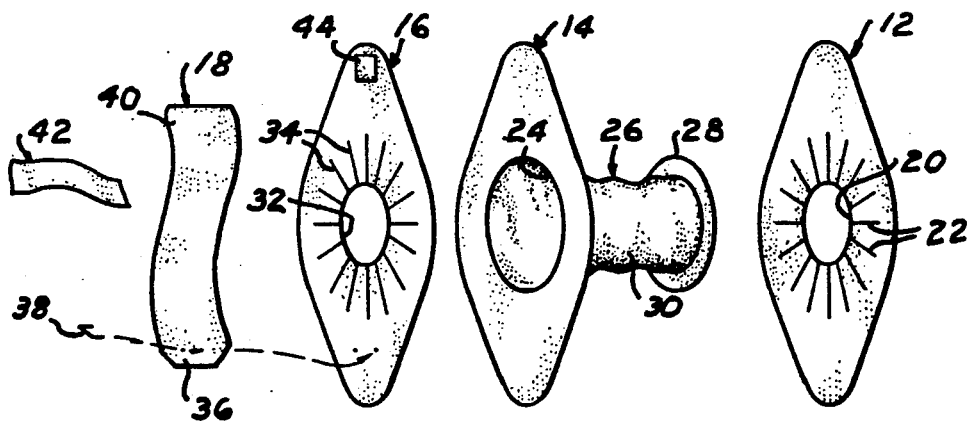
FIG. 3 is an exploded perspective view of the components forming the device.

In the drawings:

Referring first to FIGS. 1-3, the reference numeral 10 indicates the device which is flat-like and substantially ovate in front elevation. The device 10 principally comprises a front sheet 12, an intermediate or center sheet, bag 14 and a back sheet 16 having a towel 18 attached thereto.

The front sheet 12 is preferably formed from flexible sheet material having a central aperture 20 of predetermined diameter. The material around the aperture 20 is provided with a plurality of radial slits 22 angularly spaced-apart, for example at 22.5°, to permit the passage of an article of larger diameter than the aperture 22 without rupturing or tearing the material of the sheet 12.

The central sheet 14 is similarly formed from selected sheet material and of ovate shape having its major axis longitudinally aligned with the major axis of the front sheet 12. The central sheet 14 is similarly provided with a central aperture 24 of selected diameter, preferably greater than the diameter of the aperture 20 for the reason believed presently apparent.

A tube or bag 26 having an accordion pleated longitudinally compressible and expandable wall 30 is connected by its open end with the wall defining the central sheet aperture 24 with the other end of the bag provided with a circular disk 28 of similar flexible material forming an end plate for the bag 26.

The disk 28 is similarly centrally provided with a plurality (4) diametric slits 29 of less length than the diameter of the aperture 20 medially intersecting each other centrally of the disk 28 for the purposes presently explained. Diametrically the disk 28 is slightly greater than the diameter of the bag 26 (FIG. 3) and front sheet aperture 20. The flanged edge perimeter portion of the disk projecting outwardly of the bag wall 30, is interposed, in longitudinally collapsed position, between the front and center sheet inwardly of the bonded area, for the reason presently believed apparent.

The bag wall 30 is normally collapsed adjacent the forward surface of the center sheet 14 when the device is in its assembled ready to use form, illustrated by FIGS. 1 and 2.

The rearward or back sheet 16 is similarly formed from flexible sheet material ovate in shape with its major axis aligned with the axes of sheets 12 and 14. The sheet 16 is similarly provided with a central aperture 32 diametrically substantially equal with the front sheet aperture 20 and is similarly provided with a plurality of radial slits 34 spaced 22.5° and projecting outwardly from its aperture 32 a selected distance for permitting movement of an object therethrough of greater diameter than the aperture 32 without rupture of the back section 16.

The perimeter edge portions of the three sheets 12, 14 and 16, outwardly of the apertures, are bonded together.

The towel 18 is formed from any soft fabric or paper and is folded to an elongated rectangular configuration, as illustrated by FIGS. 2 and 3, and is connected at one end portion 36 as by a staple 38 extending through the towel and one end portion of the major axis of the three superposed sheets 12, 14 and 16.

The other end portion 40 of the towel is maintained adjacent the back surface of the back sheet 16 by a strap-like strip 42 of flexible sheet material extending transversely of the back sheet near its minor axis. The respective end portions of the strip 42 contacting the surface of the back sheet laterally outward of the longitudinal edges of the towel, are secured to the back sheet 16 by any suitable bonding material, not shown.

A relatively small rectangular section of double coated adhesive tape 44, or the like, is attached to the back surface of the end portion of the back sheet 16 opposite the position of the staple 38 for purpose of closing the back sheet aperture as hereinafter explained.

Operation

Figure 4:
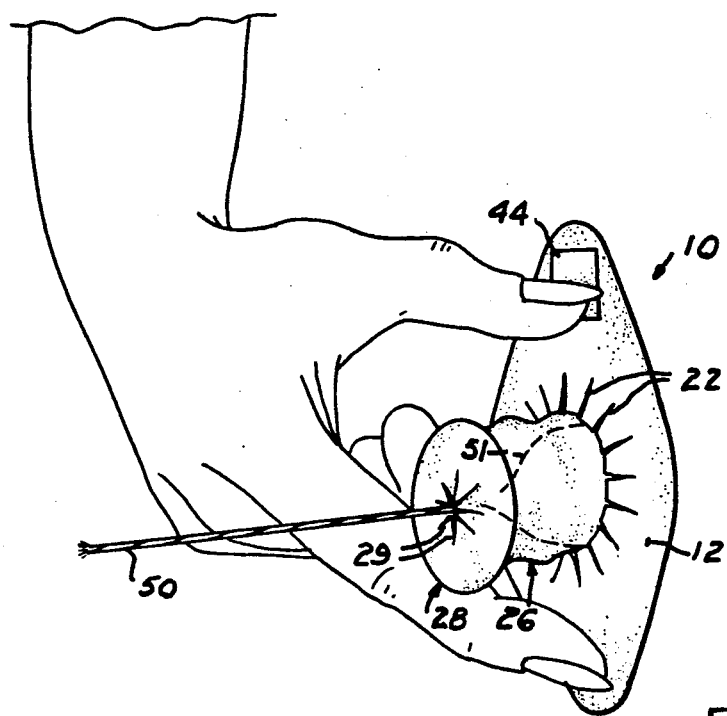
FIG. 4 is a perspective view of the device when receiving a disposable sanitary item; and, FIG. 5 is a perspective view illustrating the manner of sealing the device for final disposal with its enclosed sanitary item.
Figure 5:
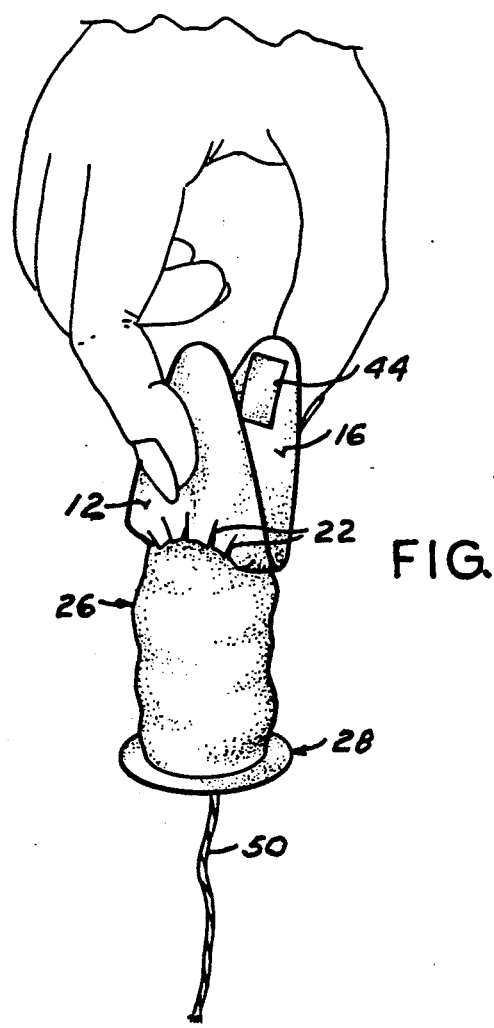

Referring also to FIGS. 4 and 5, the user of the device removes the strip 42 from the rearward surface of the back sheet 16 by manually tearing it away leaving the towel attached by the staple 38, if desired, or removing it.

The free end of a tampon string 50 is then inserted through the slits 29 in the circular disk 28.

The device 10 minus the towel 18 is then disposed, as a unit, flatly against the surface of the user's body with the central openings and slits generally centrally disposed over the cavity containing the tampon.

By holding the respective end portions of the device as by a thumb and fore finger placed on the end portions of the major axes of the ovate shape (FIG. 4), and using the other hand to pull on the string 50, the tampon 51 is withdrawn from the cavity into the bag 26 wherein the tampon contacting the circular disk 28 pulls it through the front sheet 12 by the expansion of the slitted material. As illustrated by FIG. 4, the tampon entering the bag unfolds its wall 30 to extend forwardly of the front sheet.

With the bag extended fully to its forward position, as illustrated by FIG. 3, and projecting forwardly of the front sheet 12, the major or axis end portions of the sheets are grasped and pulled in a toward each other so that the double coated tape 44 seals with the opposite major axis end flat portion of the sheet 16 to close the opening 32.

The entire unit is then placed in a suitable disposal container, ordinarily provided in restrooms and the like.

Obviously the invention is susceptible to changes or alterations without defeating its practicability. Therefore, I do not wish to be confined to the preferred embodiment shown in the drawings and described herein.

I claim:

1. A device for the removal and disposal of a sanitary item having an attached string, comprising:

a front sheet and a back sheet respectively superposed on and bonded by their perimeter edge portions to opposite sides of a center sheet;

said sheets each having a centrally disposed aperture axially aligned with the apertures in the other sheets;

container means for containing the sanitary item including a bag having an accordion pleated longitudinally expandable and collapsible wall defining one open end, the end portion of said wall adjacent the open end being secured to said center sheet around its central aperture; and, a disk axially closing the other end of said bag and releasably interposed at its peripheral edge portion between said front sheet and said center sheet around the apertures therein, said disk having a plurality of radial slits angularly spaced about its center for manually extending one end portion of said string therethrough and withdrawing a sanitary item from a cavity into said bag.

2. The device according to claim 1 in which the diameter of said bag is greater than the diameter of the respective aperture through the front and back sheets; and, said front and said back sheet each having a plurality of radial slits intersecting the sheet edge portion defining the respective aperture.

3. The device according to claim 2 and further including:

a towel removably secured to said back sheet.

* * * * *